United States Patent
Balshi et al.

(10) Patent No.: US 10,271,929 B2
(45) Date of Patent: Apr. 30, 2019

(54) DENTAL PROSTHESIS AND METHOD OF ITS PRODUCTION UTILIZING STANDARDIZED FRAMEWORK KEYS AND MATCHING PREMANUFACTURED TEETH

(71) Applicant: Global Dental Science, LLC, Scottsdale, AZ (US)

(72) Inventors: Thomas J. Balshi, Gwynedd, PA (US); Stephen F. Balshi, Chalfont, PA (US)

(73) Assignee: Global Dental Sciences, LLC, Scottsdale, AZ (US)

( * ) Notice: Subject to any disclaimer, the term of this patent is extended or adjusted under 35 U.S.C. 154(b) by 0 days.

(21) Appl. No.: 15/390,330

(22) Filed: Dec. 23, 2016

(65) Prior Publication Data
US 2017/0231728 A1 Aug. 17, 2017

Related U.S. Application Data

(63) Continuation of application No. 15/191,868, filed on Jun. 24, 2016, and a continuation of application No. 14/495,036, filed on Sep. 24, 2014, now abandoned.

(51) Int. Cl.
*A61C 13/00* (2006.01)
*A61C 13/107* (2006.01)
(Continued)

(52) U.S. Cl.
CPC ........ *A61C 13/0001* (2013.01); *A61C 8/0027* (2013.01); *A61C 8/0048* (2013.01);
(Continued)

(58) Field of Classification Search
CPC . A61C 13/102; A61C 8/0048; A61C 13/0003; A61C 13/10; A61C 13/20; Y10T 29/49567
See application file for complete search history.

(56) References Cited

U.S. PATENT DOCUMENTS

| 200,445 A | 2/1878 | Fahnestock |
| 321,847 A | 7/1885 | Peirce et al. |

(Continued)

FOREIGN PATENT DOCUMENTS

| CA | 2505892 | 5/2004 |
| CN | 1750797 | 3/2006 |

(Continued)

OTHER PUBLICATIONS

European App EP14840991.5—EPO Search Report dated Apr. 19, 2017.

(Continued)

*Primary Examiner* — Rick K Chang
(74) *Attorney, Agent, or Firm* — Derrick Harvey; Harvey Law, PC

(57) ABSTRACT

A system including a method and associated structures creates efficiencies in the manufacture of prosthetic tooth support frameworks. Pre-manufactured teeth with matching internal keys are used in the setup of a patient prototype. Each key includes a shaft, a cervical platform, a retention knob and preferably at least one channel for the expulsion of excess adhesive fluid. The cervical platforms are shaped to provide intimate contact with a base of their respective tooth. The same tooth/key pairs are then used to make a framework pattern from the setup positioning. The pattern can be cast or scanned for direct machining to produce the finished framework.

15 Claims, 17 Drawing Sheets

(51) Int. Cl.
*A61C 8/00* (2006.01)
*A61C 13/10* (2006.01)
*A61C 13/01* (2006.01)
*A61C 13/34* (2006.01)
*A61C 13/265* (2006.01)
*A61C 13/20* (2006.01)

(52) U.S. Cl.
CPC .......... *A61C 8/0054* (2013.01); *A61C 8/0062* (2013.01); *A61C 8/0066* (2013.01); *A61C 8/0078* (2013.01); *A61C 13/0003* (2013.01); *A61C 13/0004* (2013.01); *A61C 13/04* (2013.01); *A61C 13/10* (2013.01); *A61C 13/102* (2013.01); *A61C 13/2656* (2013.01); *A61C 13/34* (2013.01); *A61C 13/20* (2013.01); *Y10T 29/49567* (2015.01)

(56) References Cited

U.S. PATENT DOCUMENTS

| | | | |
|---|---|---|---|
| 711,324 A | 10/1902 | Lacy | |
| 830,887 A | 9/1906 | Robert | |
| 1,223,450 A | 4/1917 | Van Allen | |
| 1,293,627 A | 2/1919 | Bowers | |
| 1,585,348 A | 5/1926 | Hick et al. | |
| 1,652,910 A | 12/1927 | Psayla | |
| 1,714,185 A | 5/1929 | Hugh | |
| 1,863,591 A | 6/1932 | Crowell | |
| 1,914,606 A | 6/1933 | Kinna et al. | |
| 2,036,678 A | 4/1936 | White | |
| 2,107,181 A | 2/1938 | Guyton | |
| 2,398,671 A | 4/1946 | Saffir | |
| 2,418,833 A | 4/1947 | Harris et al. | |
| 2,472,492 A | 6/1949 | Saffir | |
| 2,602,997 A | 7/1952 | Clawson | |
| 2,641,835 A | 6/1953 | Greenmun | |
| 2,985,961 A | 5/1961 | Schwartz | |
| 2,994,957 A | 8/1961 | Mcleod | |
| 3,083,459 A | 4/1963 | McMurry et al. | |
| 3,241,238 A | 3/1966 | Kersten | |
| 3,335,495 A | 8/1967 | Theodore | |
| 3,458,936 A | 8/1969 | Tuccillo et al. | |
| 3,470,614 A | 10/1969 | Kelly | |
| 3,518,761 A | 7/1970 | Susman et al. | |
| 3,644,996 A | 2/1972 | Weinkle | |
| 3,667,123 A | 6/1972 | Huey | |
| 3,702,027 A | 11/1972 | Marshall et al. | |
| 3,727,309 A | 4/1973 | Huey | |
| 3,748,739 A | 7/1973 | Thibert | |
| 3,813,777 A | 6/1974 | VanHandel et al. | |
| 3,844,702 A | 10/1974 | Dimmer et al. | |
| 3,846,911 A | 11/1974 | Wichner | |
| 3,908,272 A | 9/1975 | Arnold | |
| 3,937,773 A | 2/1976 | Huffman | |
| 4,029,632 A | 6/1977 | Gross et al. | |
| 4,227,877 A | 10/1980 | Tureaud et al. | |
| 4,247,287 A | 2/1981 | Gigante | |
| 4,299,573 A | 11/1981 | Ricci | |
| 4,398,884 A | 8/1983 | Huffman | |
| 4,533,325 A | 8/1985 | Blair | |
| 4,575,340 A * | 3/1986 | Lustig .................. | A61C 8/0048 433/173 |
| 4,591,341 A | 5/1986 | Andrews | |
| 4,634,377 A | 1/1987 | Behrend | |
| 4,784,608 A | 11/1988 | Mays | |
| 4,931,016 A | 6/1990 | Sillard | |
| 2,030,102 A | 7/1991 | Lang | |
| 5,098,296 A | 3/1992 | Cullen | |
| 5,151,044 A | 9/1992 | Rotsaert | |
| 5,169,309 A | 12/1992 | Staubli et al. | |
| 5,188,529 A | 2/1993 | Luth | |
| 5,234,339 A | 8/1993 | Grigereit | |
| 5,427,906 A | 6/1995 | Hansen | |
| 5,672,305 A | 9/1997 | Kogure | |
| 5,711,668 A | 1/1998 | Huestis | |
| 5,716,214 A | 2/1998 | Lund | |
| 5,718,584 A | 2/1998 | Wong | |
| 5,775,899 A | 7/1998 | Huffman | |
| 5,833,461 A | 11/1998 | Wong | |
| 5,839,900 A | 11/1998 | Billet et al. | |
| 5,885,078 A | 3/1999 | Cagna et al. | |
| 5,934,906 A | 8/1999 | Phimmasone | |
| 6,030,218 A | 2/2000 | Robinson | |
| 6,056,547 A | 5/2000 | Names | |
| 6,116,070 A | 9/2000 | Oshida | |
| 6,126,445 A | 10/2000 | Willoughby | |
| 6,139,322 A | 10/2000 | Liu | |
| 6,149,427 A | 11/2000 | Van Handel | |
| 6,224,372 B1 | 5/2001 | Ibsen et al. | |
| 6,227,851 B1 | 5/2001 | Chishti | |
| 6,257,895 B1 | 7/2001 | Oestreich | |
| 6,384,107 B2 | 5/2002 | Liu | |
| 6,422,864 B1 | 7/2002 | Glatt | |
| 6,488,503 B1 | 12/2002 | Lichkus et al. | |
| 6,616,444 B2 | 9/2003 | Andreiko et al. | |
| 6,788,986 B1 | 9/2004 | Traber et al. | |
| 6,814,575 B2 | 11/2004 | Poirier | |
| 6,851,949 B1 | 2/2005 | Sachdeva | |
| 7,021,934 B2 | 4/2006 | Aravena | |
| 7,153,135 B1 | 12/2006 | Thomas | |
| 7,234,940 B2 | 6/2007 | Weissman | |
| 7,433,810 B2 | 10/2008 | Pavloskaia et al. | |
| 7,474,932 B2 | 1/2009 | Geng | |
| 7,530,810 B2 | 5/2009 | Clement | |
| 7,653,455 B2 | 1/2010 | Cinader, Jr. | |
| 7,704,076 B2 | 4/2010 | Mullaly | |
| 7,758,345 B1 | 6/2010 | Christensen | |
| 7,758,346 B1 | 7/2010 | Letcher | |
| 7,806,691 B2 | 10/2010 | Berger | |
| 7,854,611 B2 | 12/2010 | Yau et al. | |
| 7,901,209 B2 | 3/2011 | Saliger et al. | |
| 7,909,607 B2 | 3/2011 | Yau et al. | |
| 7,950,924 B2 | 5/2011 | Brajnovic | |
| 8,043,091 B2 | 10/2011 | Schmitt | |
| 8,348,669 B1 | 1/2013 | Schmitt | |
| 8,567,408 B2 | 10/2013 | Roettger | |
| 8,641,938 B2 | 2/2014 | Howe | |
| 8,801,431 B2 | 8/2014 | Thompson et al. | |
| 8,875,398 B2 | 11/2014 | Balshi et al. | |
| 9,055,993 B2 | 6/2015 | Grobbee et al. | |
| 9,155,599 B2 | 10/2015 | Thompson et al. | |
| 9,213,784 B2 | 12/2015 | Thompson et al. | |
| 9,364,302 B2 | 6/2016 | Thompson et al. | |
| 9,402,698 B2 | 8/2016 | Thompson et al. | |
| 9,717,572 B2 | 8/2017 | Thompson et al. | |
| 9,744,010 B2 | 8/2017 | Grobbee | |
| 2002/0015934 A1 | 2/2002 | Rubbert et al. | |
| 2002/0180760 A1 | 12/2002 | Rubbert et al. | |
| 2003/0108845 A1 | 6/2003 | Giovannone | |
| 2003/0138756 A1 | 7/2003 | Monkmeyer | |
| 2003/0162147 A1 | 8/2003 | Dequeker | |
| 2003/0163291 A1 | 8/2003 | Jordan et al. | |
| 2003/0211444 A1 | 11/2003 | Andrews | |
| 2004/0005530 A1 | 1/2004 | Mullaly | |
| 2004/0029068 A1 | 2/2004 | Sachdeva et al. | |
| 2004/0185422 A1 | 9/2004 | Orth et al. | |
| 2004/0219490 A1 | 11/2004 | Gartner et al. | |
| 2005/0175957 A1 | 8/2005 | Haje et al. | |
| 2005/0186539 A1 | 8/2005 | McLean | |
| 2005/0284489 A1 | 12/2005 | Ambis | |
| 2006/0040232 A1 | 2/2006 | Shoup | |
| 2006/0040236 A1 | 2/2006 | Schmitt | |
| 2006/0063135 A1 | 3/2006 | Mehl | |
| 2006/0210945 A1 | 9/2006 | Savic et al. | |
| 2006/0286507 A1 | 12/2006 | Dequeker | |
| 2007/0154868 A1 | 7/2007 | Scharlack et al. | |
| 2007/0190492 A1 | 8/2007 | Schmitt | |
| 2007/0231774 A1 | 10/2007 | Massad | |
| 2008/0085489 A1 | 4/2008 | Schmitt | |
| 2008/0090207 A1 | 4/2008 | Rubbert | |
| 2008/0127698 A1 | 6/2008 | Luckey et al. | |
| 2008/0206710 A1 | 8/2008 | Kruth et al. | |
| 2008/0206714 A1 | 8/2008 | Schmitt | |

(56) References Cited

U.S. PATENT DOCUMENTS

| | | |
|---|---|---|
| 2008/0209974 A1 | 9/2008 | Ewolski et al. |
| 2008/0228303 A1 | 9/2008 | Schmitt |
| 2008/0300716 A1 | 12/2008 | Kopelman |
| 2009/0081618 A1 | 3/2009 | Lamar |
| 2009/0143609 A1 | 6/2009 | Araya |
| 2009/0148813 A1 | 6/2009 | Sun et al. |
| 2009/0162813 A1 | 6/2009 | Glor |
| 2009/0181346 A1 | 7/2009 | Orth |
| 2009/0287332 A1 | 11/2009 | Adusumilli et al. |
| 2009/0291407 A1 | 11/2009 | Kuo |
| 2009/0325125 A1 | 12/2009 | Diangelo et al. |
| 2010/0015572 A1 | 1/2010 | Dierkes et al. |
| 2010/0062394 A1 | 3/2010 | Jones et al. |
| 2010/0086186 A1 | 4/2010 | Zug et al. |
| 2010/0094446 A1 | 4/2010 | Baloch et al. |
| 2010/0105011 A1 | 4/2010 | Karkar et al. |
| 2010/0324875 A1 | 12/2010 | Kalili |
| 2011/0045442 A1 | 2/2011 | Adusimilli |
| 2011/0112804 A1 | 5/2011 | Chishti et al. |
| 2011/0129796 A1 | 6/2011 | Riggio |
| 2011/0236856 A1 | 9/2011 | Kanazawa et al. |
| 2011/0244417 A1 | 10/2011 | Hilsen et al. |
| 2012/0058449 A1 | 3/2012 | Sklarski et al. |
| 2012/0094253 A1 | 4/2012 | Berger |
| 2012/0095732 A1 | 4/2012 | Fisker et al. |
| 2012/0100500 A1 | 4/2012 | Gao |
| 2012/0178045 A1 | 7/2012 | Massad |
| 2012/0179281 A1 | 7/2012 | Steingart et al. |
| 2012/0258426 A1 | 10/2012 | Boe |
| 2012/0285019 A1 | 11/2012 | Schechner et al. |
| 2012/0329008 A1 | 12/2012 | Fishman et al. |
| 2013/0101962 A1 | 4/2013 | Howe |
| 2013/0108988 A1 | 5/2013 | Simoncic |
| 2013/0167380 A1 | 7/2013 | Balshi |
| 2013/0209962 A1 | 8/2013 | Thompson et al. |
| 2013/0216978 A1 | 8/2013 | Thompson et al. |
| 2013/0218532 A1 | 8/2013 | Thompson et al. |
| 2013/0221554 A1 | 8/2013 | Jung et al. |
| 2013/0249132 A1 | 9/2013 | Thompson et al. |
| 2013/0280672 A1 | 10/2013 | Thompson et al. |
| 2013/0316302 A1 | 11/2013 | Fisker |
| 2013/0337412 A1 | 12/2013 | Kwon |
| 2014/0045967 A1 | 2/2014 | Thomas et al. |
| 2014/0099600 A1 | 4/2014 | Harrison |
| 2014/0272796 A1 | 9/2014 | Grobbee et al. |
| 2015/0010885 A1 | 1/2015 | Balshi et al. |
| 2015/0037760 A1 | 2/2015 | Thompson et al. |
| 2015/0064653 A1 | 3/2015 | Grobbee et al. |
| 2015/0134094 A1 | 5/2015 | Thompson et al. |
| 2015/0230891 A1 | 8/2015 | Grobbee et al. |
| 2015/0245891 A1 | 9/2015 | Grobbee |
| 2015/0245892 A1 | 9/2015 | Grobbee |
| 2016/0374778 A1 | 12/2016 | Grobbee |
| 2017/0112599 A1 | 4/2017 | Balshi |

FOREIGN PATENT DOCUMENTS

| | | |
|---|---|---|
| EP | 1062916 | 12/2000 |
| EP | 1252867 | 10/2002 |
| EP | 2915503 | 7/2016 |
| FR | 2035133 | 12/1970 |
| JP | 2008307281 | 12/2008 |
| WO | WO 2001032096 | 12/2001 |
| WO | WO 2003024352 | 3/2003 |
| WO | WO 2004060197 | 7/2004 |
| WO | WO2009105661 | 8/2009 |
| WO | WO 2009105700 | 8/2009 |
| WO | WO 2010022479 | 3/2010 |
| WO | WO 2012030493 | 3/2012 |
| WO | WO 2012041329 | 4/2012 |
| WO | WO 2012061652 | 5/2012 |
| WO | WO 2012061659 | 5/2012 |
| WO | WO 2012061660 | 5/2012 |
| WO | WO 2012064655 | 5/2012 |
| WO | WO 2014130536 | 8/2014 |
| WO | WO 2014159436 | 10/2014 |
| WO | WO 2015063032 | 3/2015 |

OTHER PUBLICATIONS

PCT App PCTUS2014051008—International Search Report and Written Opinion dated Nov. 20, 2014.

PCT App PCTUS201451008—Preliminary Report on Patentability dated Mar. 1, 2016.

Positioning handle and occlusal locks for the Teeth-in-a-Day protocol:, The Journal of Prosthetic Dentistry, 2016, Balshi et al., p. 274-278.

"A New Protocol for Immediate Functional Loading of Dental Implants", Dentistry Today, Balshi et al., Sep. 2001, vol. 20, No. 9.

U.S. Appl. No. 13/343,566—Restrictriction Requirement dated Apr. 16, 2014.

U.S. Appl. No. 13/343,566—Notice of Allowance dated Jun. 26, 2014.

U.S. Appl. No. 14/013,295—Non-Final Official Action dated Dec. 19, 2014.

U.S. Appl. No. 14/495,036—Non-Final Official Action dated May 19, 2015.

U.S. Appl. No. 14/495,036—Final Official Action dated Nov. 6, 2015.

U.S. Appl. No. 14/495,036—Final Official Action dated Jun. 7, 2016.

U.S. Appl. No. 14/698,649—Non-Final Official Action dated Sep. 26, 2017.

U.S. Appl. No. 14/013,295—Notice of Allowance dated Apr. 13, 2015.

U.S. Appl. No. 15/181,032—Non-Final Official Action dated Jul. 6, 2017.

U.S. Appl. No. 15/191,868—Non-Fial Official Action dated Jun. 16, 2017.

U.S. Appl. No. 15/390,330—Non-Final Official Action dated Jun. 1, 2017.

* cited by examiner

DENTAL PROSTHESIS AND METHOD OF
ITS PRODUCTION UTILIZING
STANDARDIZED FRAMEWORK KEYS AND
MATCHING PREMANUFACTURED TEETH

RELATED APPLICATION

This patent application is a continuation of co-pending application Ser. No. 15/191,868 entitled "DENTAL PROSTHESIS AND METHOD OF ITS PRODUCTION UTILIZING STANDARDIZED FRAMEWORK KEYS AND MATCHING PREMANUFACTURED TEETH" filed Jun. 24, 2016 and a continuation of co-pending patent Ser. No. 14/495,036 filed Sep. 24, 2014, entitled "DENTAL PROSTHESIS AND METHOD OF ITS PRODUCTION UTILIZING STANDARDIZED FRAMEWORK KEYS AND MATCHING PREMANUFACTURED TEETH", which is a divisional of patent application Ser. No. 13/343,566, now U.S. Pat. No. 8,875,398, entitled "Dental Prosthesis and Method of its Production Utilizing Standardized Framework Keys and Matching Premanufactured Teeth" filed Jan. 4, 2012, priority from which is hereby claimed.

FIELD OF THE INVENTION

The present invention relates to frameworks for dental implant-supported prostheses produced either by conventional dental laboratory procedures including CAD/CAM or by virtual technology. More specifically, it relates to a framework using a uniquely designed set of prosthetic teeth and internal abutments specific to the individual tooth position.

BACKGROUND OF THE INVENTION

A framework for a dental prosthesis as shown in FIG. 4 is a unified metal or ceramic base structure consisting of a horizontal beam on which vertical posts, specific to the teeth they support are rigidly connected. This framework can be supported by dental implants placed in the jawbone. Such a framework is securely fixed to the jaw by screwing or cementing it onto the implants. The framework supports the specifically designed replacement teeth which are fused to the posts of the framework with a luting cement. The prosthesis containing this framework is patient-specific and must meet the strict requirements of accuracy to reach an optimal fit at the prosthesis/implant interface to distribute chewing and grinding forces appropriately to the underlying jawbone and avoiding high stresses to the underlying bone which could cause implants to deintegrate from the bone. The fit of the framework to the supporting implants should be 50 microns or less. Because the framework is capable of replacing all the teeth in a dental arch, and because the framework connects the occlusal surfaces of the replacement teeth to the osseointegrated dental implants, the dimensions of the framework are generally larger in comparison to traditional dental prostheses like crowns and tooth-supported bridges. The framework is designed to support not only replacement teeth but also the bone and gum tissue that previously immediately surrounded the missing teeth.

The traditional or conventional dental laboratory method for creating these frameworks is based on the manual design of a physical model of the framework in wax or resin and the production of the framework by means of lost wax casting or copy milling. These previous methods of framework production can be highly precise however they require very skilled dental laboratory technicians doing time-consuming modeling of the frame, a process that is inefficient and costly. The traditional lost wax process is very lengthy and highly labor intensive, consisting of many manual steps that include the design, manual contour and fabrication of the wax pattern, investing the pattern in a refractory mold, melting and evaporating the wax pattern in a high temperature burn out oven over many hours, melting the metal and casting it into the pattern mold, devesting the solidified metal framework and refining the surface of the framework to permit the next phase to begin. A current alternative to the lost wax casting method of framework construction is the use of CAD/CAM technology to scan the wax or resin pattern frame and robotic ally mill a precise copy of the pattern. Framework production by virtual technology is available but its ability to create tooth support mechanisms is limited.

Following completion of the metal or ceramic framework, impressions of that framework are made and stone casts are produced to replicate the metal framework. These casts are then cut into sections providing individual stone dies being replicas of the vertical tooth support portion of the framework pattern, upon which individual teeth are manually created from wax relying on the artistic skill of the dental technician. These individual teeth may then be either scanned or copy milled in a tooth colored material. These steps of custom fabrication of the individual prosthetic teeth are eliminated by the present invention thus avoiding time-consuming and highly skilled labor required of the dental technicians and ceramists. Furthermore, later if a tooth needs to be replaced because it has become worn or chipped, the above-described process must be repeated to provide a replacement for that tooth. There is therefore a need in the dental arts for a method of prosthesis production which is less time-consuming and labor-intensive and which requires less skill. Further, there is a need for such a system which can also provide the highest quality result for the patient.

SUMMARY OF THE INVENTION

In order to meet the needs in the art described above, the present invention has been devised which for the first time provides a rapid and precisely accurate method of prosthesis production that is highly repeatable, requiring limited technical ability by dental technicians.

This is achieved by a simplified system for the production of the final implant-supported prosthesis by using the identical tooth set that was used at or shortly after the surgical placement of the implants for the provisional temporary prosthesis. By using the identical tooth set of the final prosthesis, the provisional prosthesis becomes the prototype for the position of the teeth in the final prosthesis. This position can be recorded manually with a variety of indices or virtually by scanning the provisional teeth. In an optional more advanced adaptation of the invention, individual tooth data files can be incorporated into software systems to accelerate the process by virtual construction of the framework followed by CNC copy milling. It also provides "off the shelf" future replacement teeth that will fit the vertical framework supports precisely should tooth wear or fracture occur with patient natural function.

As further described in greater detail herein, the present invention provides premanufactured prosthetic teeth available in resin, ceramic, or wax, with highly specific and precise matching internal struts (hereinafter "keys") that are use to support the teeth when affixed to the horizontal beam of the unified framework. Once the tooth arrangement selected from a library of individual teeth has been determined to be positioned appropriately for individual patient function and appearance, this setup position of the teeth is recorded either physically or digitally. Based on the position of the teeth with the vertical keys still occupying each individual tooth (hereafter "keyed teeth"), the keyed teeth pairs are easily and quickly connected to the horizontal beam during its formation with a wax or resin or connected virtually in a computer design system containing the specific files for the tooth matching vertical keys.

Once the properly positioned keyed teeth have the keys attached to the horizontal beam, the teeth are removed from the keys revealing the completed pattern. This pattern, either wax or resin, can then be invested and cast using traditional dental laboratory methods, or it can be scanned and the file transmitted to a CNC milling machine for the production of the metal or ceramic framework. Whether cast or milled, the present framework is composed of a very rigid and highly precise metal or ceramic that is biocompatible and capable of resisting complex heavy loading forces applied to the specific individual teeth, providing long term functionality required by implant-supported prostheses.

When the framework is completed, the previous set of keyway teeth can be installed onto the framework and fused to the frame with a luting cement. The prosthesis is then completed with the application of pink gingival resin or composite material. Replacement of teeth on the framework will be precise and accurate due to the high level of fit of the individual teeth to the vertical keys.

In general terms the invention may be described as a method for producing a prosthetic tooth support framework including a horizontal beam, vertical support struts and implant prosthetic connectors comprising the steps of:

constructing a working model of at least a portion of a human dental arch;

arranging pre-manufactured teeth on said model to create a prototype setup representing a finished prosthesis, said teeth each including an axial internal keyway for receiving a key;

inserting a plurality of keys into a closely fitting keyway of the teeth forming keyed tooth pairs, an attachment portion of each key extending from a base of each tooth;

holding said keyed tooth pairs in a setup location adjacent a dental arch defined by said
model, said model including implant prosthetic connectors;

affixing said key attachment portions onto a horizontal beam and said implant prosthetic connectors while held in said setup location during the formation of a beam assembly;

removing the teeth from the beam assembly leaving a framework pattern; and constructing a finished prosthetic tooth framework using said beam assembly as a pattern, the pattern keys each matching the configuration and location of the permanent teeth support struts of said finished framework.

The present invention may comprise a free-standing one-piece key utilized in forming a pattern for a prosthetic framework strut that may be affixed upon one or more implants or implant abutments within a prosthetic tooth, the key comprising a shaft having a coronal aspect at a coronal end of the shaft, a retention knob at an opposite end of the coronal end, the retention knob having a width greater than that of the shaft and the shaft at the coronal end being configured to fit within a socket of a tooth comprising an axial internal keyway, a cervical platform between the retention knob and the coronal end, and comprising a supporting base of the key, the cervical platform further having circumference configured to support a cervical aspect of the tooth. The key may include an elongate channel extending along a surface of the shaft to cervical platform for the expulsion of excess adhesive fluid, wherein said channel may be an axial groove that forms a release opening at a margin between the tooth and the cervical platform, forming a release opening at a margin between the tooth and the cervical platform. The shaft may inwardly tapered from said platform toward the coronal aspect of the key. The retention knob of the key may be a spheroid or other shapes that are greater than diameter or width of the shaft. The shaft may resemble a triangular prism.

The present invention may further comprise a vertical strut component to be disposed between a prosthetic framework model and a socket of a prosthetic tooth socket, the strut comprising an elongate shaft having a coronal aspect at a first end of the shaft, a retentive element at a second end of the shaft, the retention element having a width greater than that of the shaft so that it may be mechanically fitted within a prosthetic frame work model, and the coronal aspect being configured to fit within a socket of a tooth comprising an axial internal keyway, a cervical platform between the first and second end having a width greater than the shaft and being configured to support a cervical aspect of the prosthetic tooth, an elongate channel extending along a surface of the shaft to cervical platform for the expulsion of excess adhesive fluid, wherein said channel is an axial groove that forms a release opening at a margin between the tooth and the cervical platform. The shaft may comprise a second elongate channel on an opposite side of the shaft, so that a cross-section of the shaft having an elongate channel and a second elongate channel generally resembles the letter This prosthesis construction has many advantages over traditional dental laboratory methods for framework production. These advantages include but are not limited to the following: 1) significant reduction in the time for the labor intense design, 2) fabrication of the framework pattern is simplified by the use of the keys due to the use of standardized key way teeth, 3) technician skill required is reduced due to the simplified pattern fabrication, and 4) maintenance of the implant-supported prosthesis is easier because the replacement teeth are cataloged and the replacement teeth can still be modified or customized to meet specific patient requirements.

Accordingly, it is the main object of the present invention to provide a procedure and method for the production of a high-strength biocompatible dental implant-supported framework with individually specific vertical keys to support sets of individual prosthetic teeth in a timesaving and labor-saving system.

It is a further objective to produce these frameworks manually with traditional dental laboratory (lost wax), copy milled or constructed virtually so that the resultant framework will have a precision fit to the implants of less than 50 microns.

It is another object of the present invention is to offer a diversified system that consists of prosthetic teeth in various shapes, sizes and colors that can be used with a manually built framework pattern.

Another object of the present invention is to provide an implant-supported prosthesis that permits the cementation of selected prefabricated teeth onto a framework, thereby eliminating the custom fabrication of individual teeth by dental technicians.

Yet another object of the present invention is to provide a method of easy tooth replacement in the future for patients who have worn or chipped a tooth or a portion of the prosthesis through natural function or accidental trauma.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 12b shows the final casting resulting from the pattern of FIG. 12a.

DESCRIPTION OF THE PREFERRED EMBODIMENT

Figure 1A:
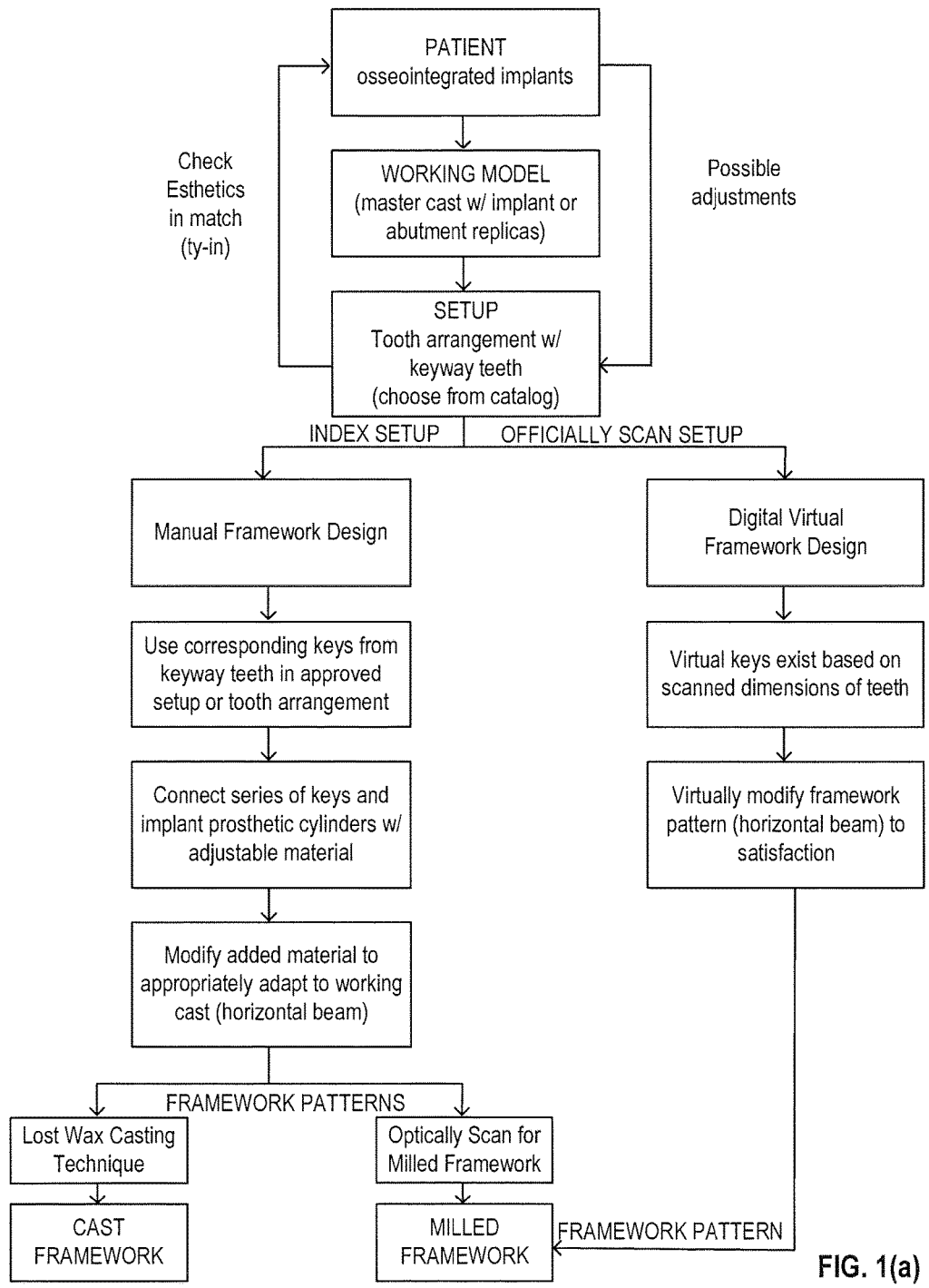
FIG. 1a is a diagram showing the process of utilizing the invention.
Figure 1B:
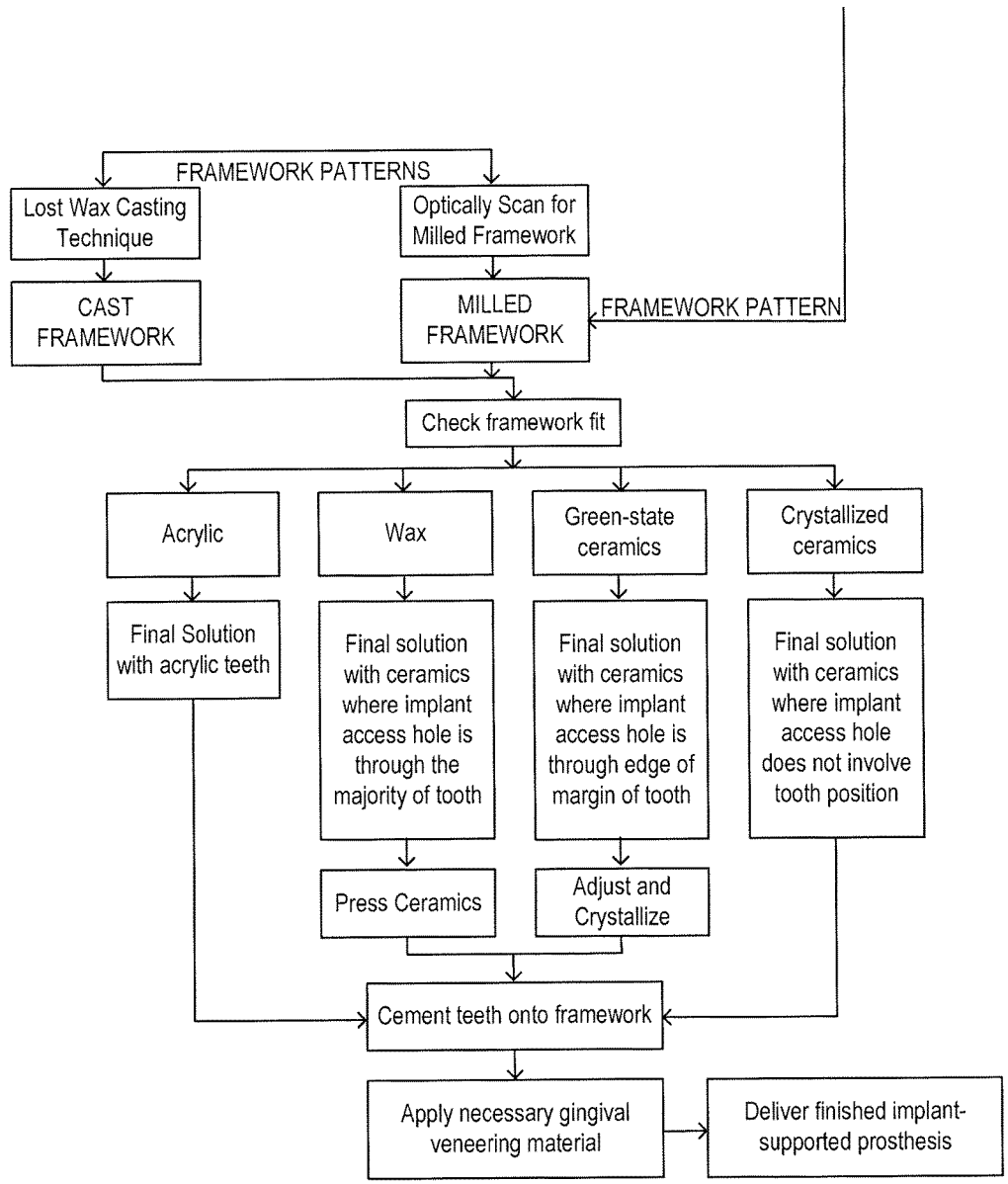
FIG. 1b is a diagram showing the process of utilizing the invention.
Figure 2:
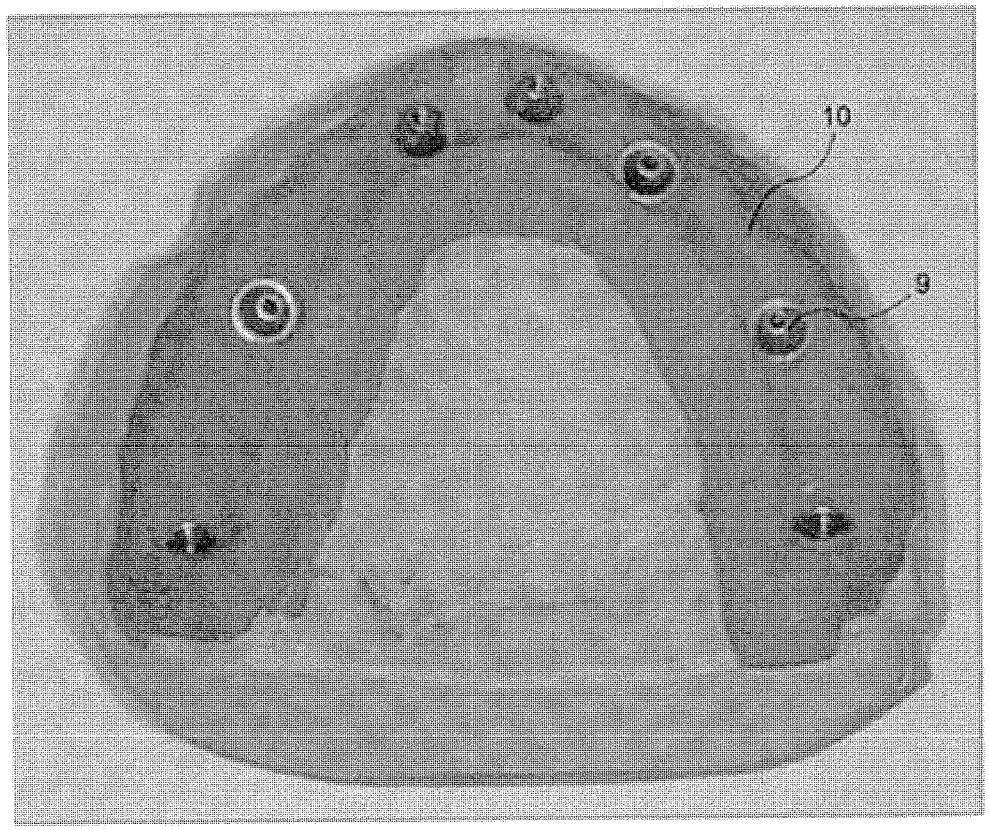
FIG. 2 is a top rear isometric view of a patient model.
Figure 3:
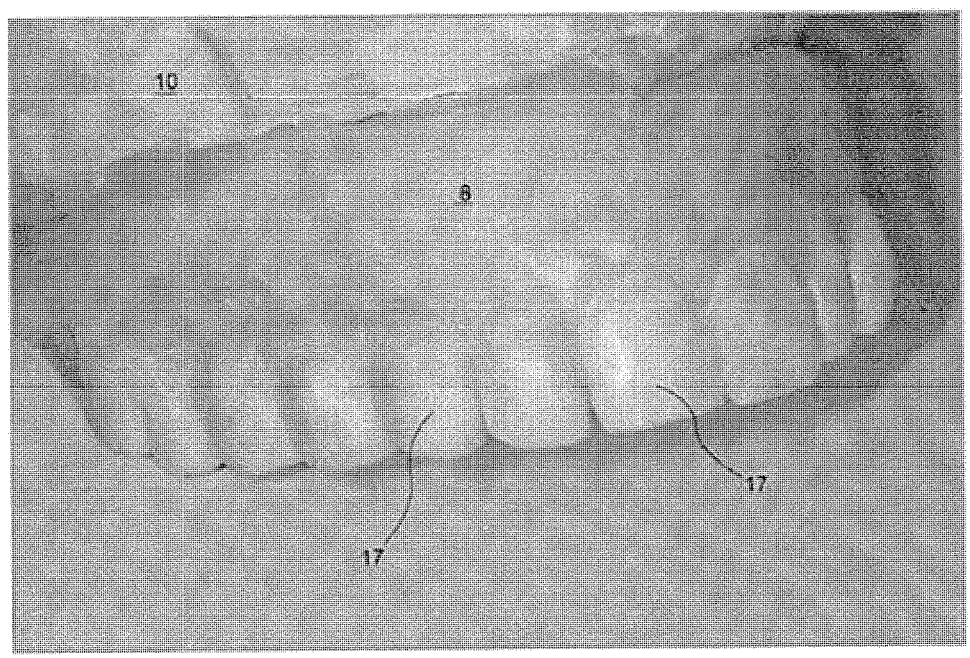
FIG. 3 is a left side elevation view of a prototype setup built on the model.

A step-by-step process showing the methodology and use of the novel structures comprising the invention is depicted in FIG. 1. Referring now to FIG. 2, the process begins as in current practice with the patient first receiving osseointegrated implants. From an impression of the implants including connectors, a working cast or model 10 is produced. As depicted in FIG. 3, a setup using keyway teeth 17 built on the completed working model 10 can be kept in the mouth of the patient for possible adjustments. This completes a prototype of the finished prosthesis. This is similar to current practice but with the use of novel keys and keyway teeth to form the setup, which keys and keyway teeth then are used to construct the vertical struts of the framework in the next steps of the invention. These further steps comprise designing a tooth-supporting framework which includes vertical keys positioned to hold their respective keyway teeth prescribed by the setup.

Figure 4:
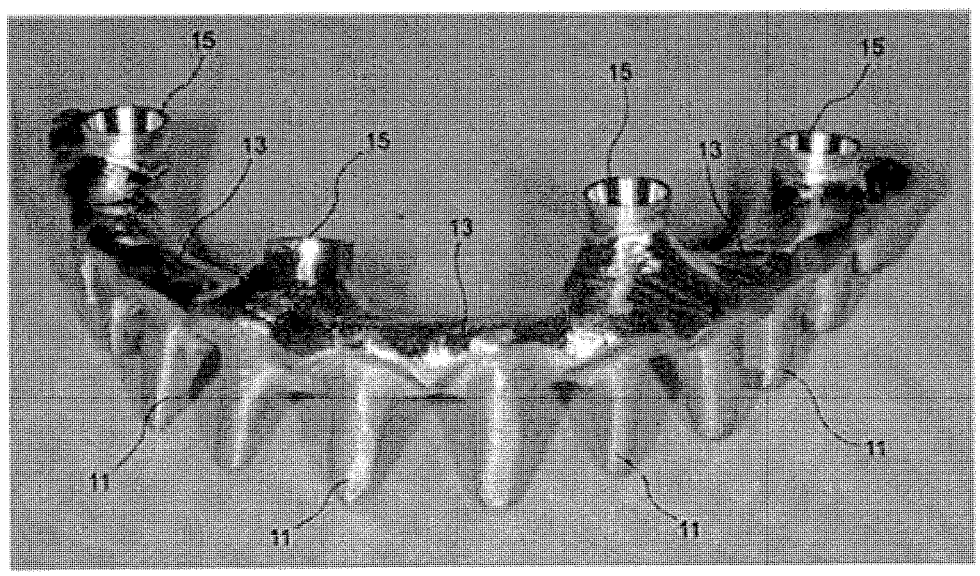
FIG. 4 is a top front isometric view of a typical dental prosthetic framework.

Referring now to FIG. 4, one goal of the invention is to produce a framework of this type. The basic elements of the inventive framework are the keys 11, a supporting horizontal beam 13 and implant connectors, in this example, cylinders 15 on the opposite side of the beam. The horizontal beam 13 is an intermediate connecting structure in the framework pattern or final frame, either metal or ceramic, parallel to the bite plane that unites the vertical keys supporting the teeth on one side and the implant prosthetic cylinders that connect underlying dental implants on the other side. The construction of the implant side of the horizontal beam follows current practice and therefore need not be discussed in detail. As further described herein, the main features of the invention are the keyway teeth and keys and the method by which they are employed to create the teeth-supporting abutments of a finished framework.

Figure 5:
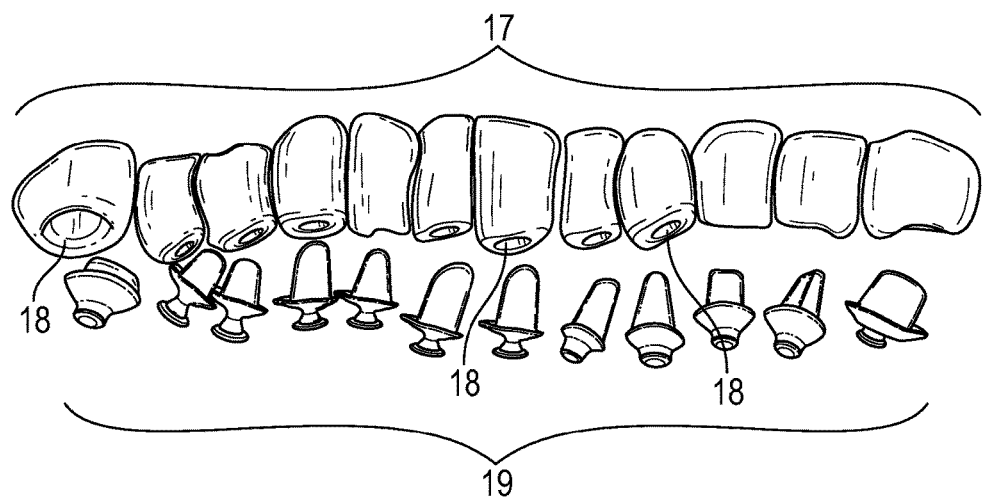
FIG. 5 is a front isometric view showing a full set of keys and keyway teeth.

Referring now to FIG. 5, the keyway teeth 17 of the invention are full anatomic prosthetic teeth made of a variety of materials such as acrylic resin, composite, ceramic or wax. They are specifically designed for implant-supported prosthesis and are catalogued in a similar way that denture teeth are used in current fixed and removable prosthetics. Keyway teeth are so named because they have specific vertical keyways or sockets 18 inside the teeth which intimately receive specially designed pattern keys 19 as further described below and as shown in FIGS. 6a and 6b and FIGS. 7a, 7b and 7c.

The keyway teeth are preferably coated with an opaque layer for color control and are cataloged in various shapes and sizes available in numerous shades (colors) just as any traditional denture tooth line. Each different tooth geometry is provided in the above materials.

The position of the prosthetic screw access channel may dictate the selection of the material used for a given keyway tooth position. By way of example, if the prosthetic screw access channel is directly through the occlusal table of the molar, it may be advantageous to use the wax version of that keyway tooth. The wax keyway tooth can be modified with a hole to provide direct access to the prosthetic retention screw. After modification, the wax version of the keyway tooth can be invested and finalized with a pressed ceramic. In another example, if the prosthetic screw access channel impinges on the cervical margin of the keyway tooth, it may be advantageous to use the green state tooth with appropriate marginal adaptation to accommodate the screwdriver access to the retention screw. Following adaptation would be the crystallization of the green state to a solid ceramic keyway tooth. The keyway teeth also have a cervical groove 50 to aid in retention as a mechanical interlock with the gingival veneering material once the tooth is luted to the framework in a final step in the process shown in FIG. 13.

Figure 6A:
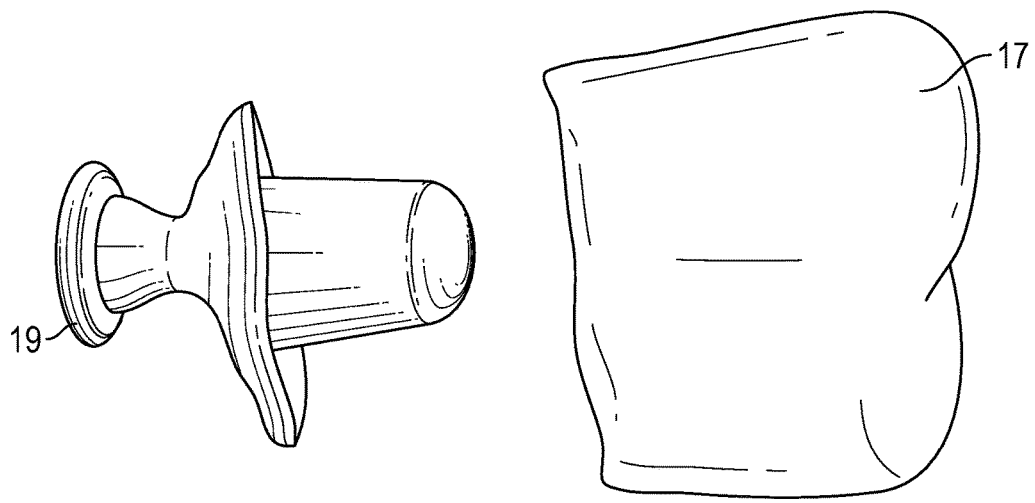
FIGS. 6a and 6b are elevation views showing the assembly of a keyed tooth pair.
Figure 6B:
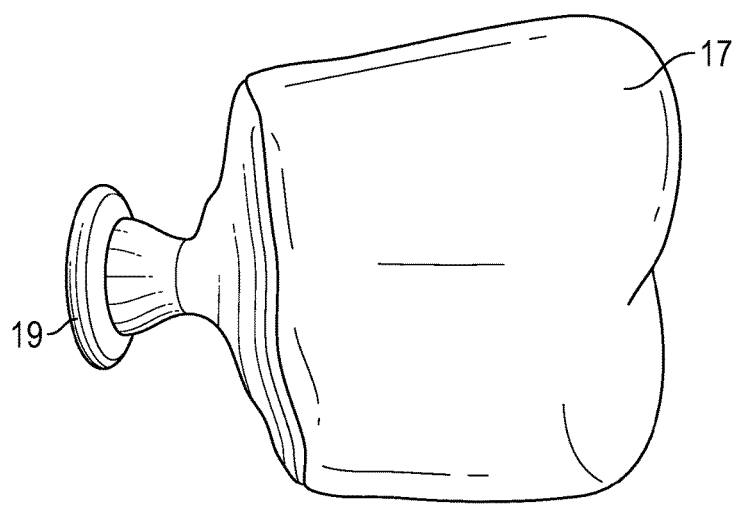
Figure 7A:
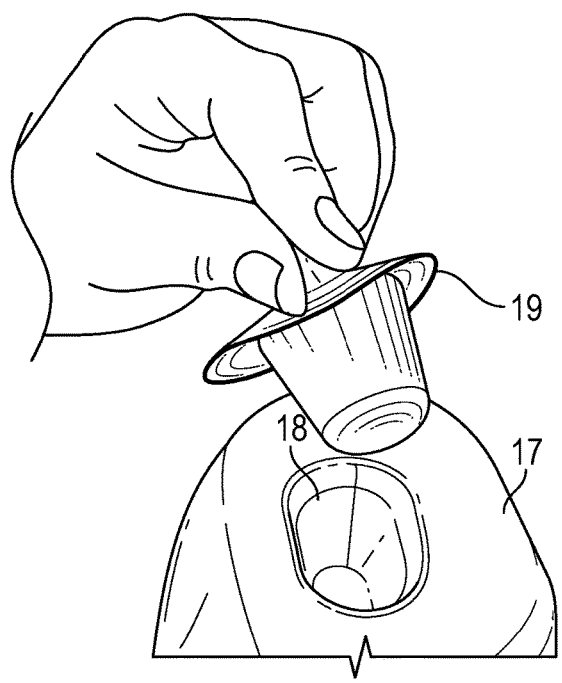
FIGS. 7a, 7b and 7c are isometric views showing detail of the keys.
Figure 7B:
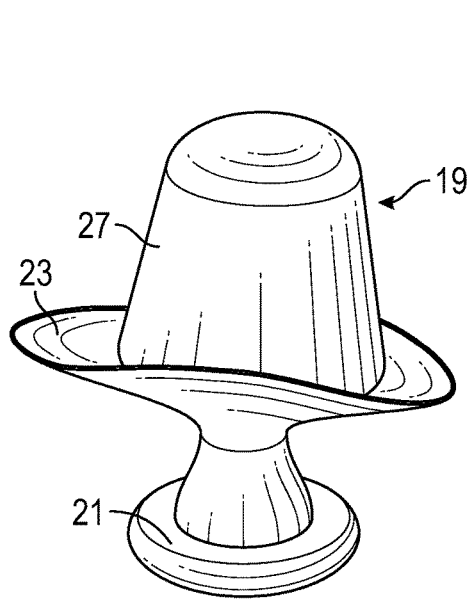
Figure 7C:
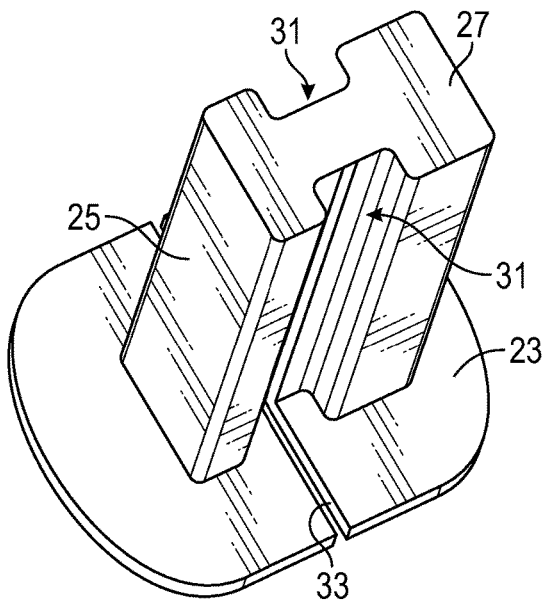

As shown in FIGS. 6a and 6b and with further detail in FIGS. 7a, 7b and 7c, the pattern keys 19 are vertical struts of various configurations that each fit precisely within the socket of a designated keyway tooth 17. The pattern keys are one of the most important aspects of the present invention. They comprise the following structural features: a retention knob 21 at a base end, a cervical platform 23 adjacent the retentive knob and an elongate tapered shaft 25 extending axially from the platform terminating at an opposite end 27 forming the coronal aspect of the key. The shaft is tapered from the cervical platform to the coronal aspect for optimal cement retention of the keyway tooth. As shown in FIG. 7c, the shaft preferably includes at least one cement release channel 33 which are formed by one or more axial grooves which lie along opposing surfaces of the shaft. Two channels are depicted in this embodiment (31, 33). This embodiment depicts an "H" cross section configuration of the shaft, however it should be understood that various shapes may be employed so long as there are no sharp edges along the surface of the key. The cement release channels run from the coronal aspect of the key to the edge of the cervical platform. The purpose of the channel(s) is to relieve hydraulic back pressure and permit the expulsion of flowable cement or other luting agents when the keyway tooth is fastened to the final unifying framework. The cervical platform 23 is the supporting base of the key that supports the cervical aspect of each keyway tooth. Incorporated into the lingual aspect of the platform is a portion of the cement release channel 33. The platforms shown are concave but may be any shape so long as it provides an intimately mating surface with the base of the tooth. The retentive knob provides a structural linkage to the horizontal beam by molding into the beam material as it is being formed. The keys are anti-rotational inside the keyway teeth so that only one position of fit exists. The keys are preferably made of a moldable and adjustable material that is chemically compatible with traditional resins and composites when they are connected to adjacent keys and the implant prosthetic cylinders to build the horizontal beam. The junction of all geometric planes of the keys should be round, avoiding any sharp angles.

One of the main advantages of the present invention is that it can utilize more commonplace dental laboratory skills and equipment or alternatively can be utilized with technologically advanced optical scanning. This makes the invention available to the greatest number of users. This more commonplace practice will now be discussed.

Figure 8:
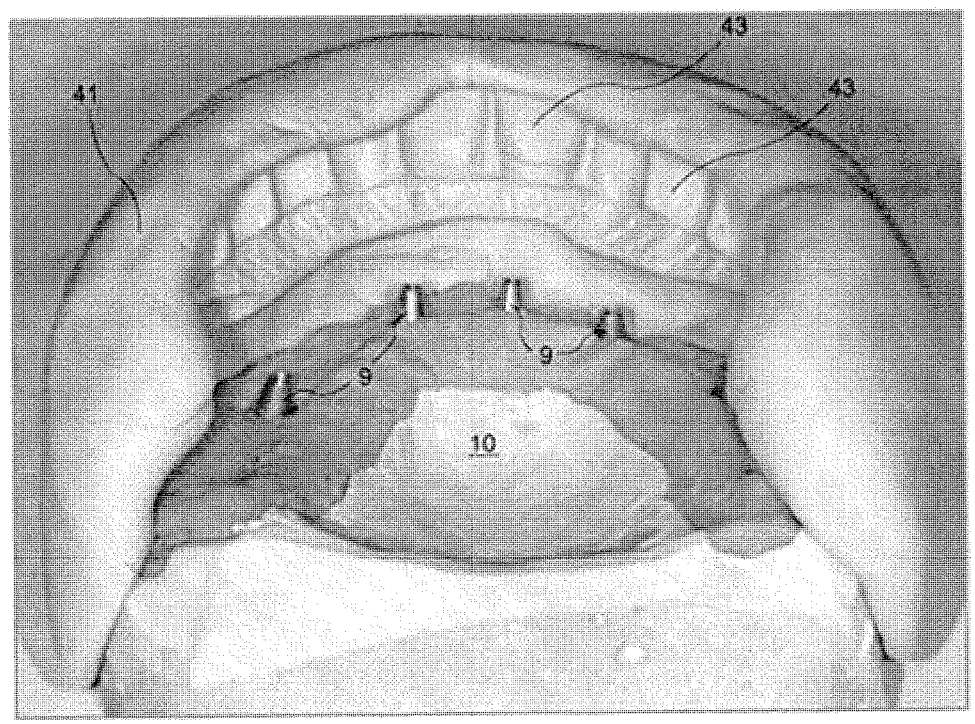
FIG. 8 is a rear view showing a matrix impression taken from the model and setup.

Once the tooth setup position has been determined, that position is recorded manually with laboratory indices or virtually in computer programming to dictate the position of the individual teeth and keys as depicted in the layout shown in FIG. 3. An impression is then taken of the setup to create a facial matrix 41 positioned on the model 10 as shown in FIG. 8.

Figure 9:
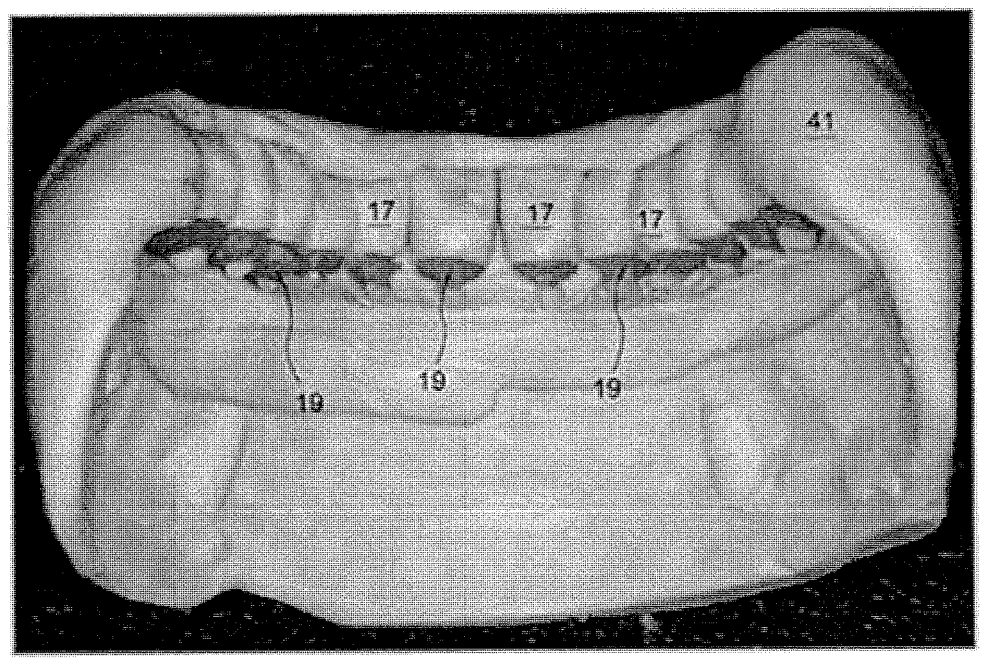
FIG. 9 is a rear view showing keyed teeth held in the matrix.

The matrix has pockets 43 that can hold each of their respective teeth in its proper position while leaving the bottom portions of the teeth exposed as shown in FIG. 9. During this step in the process, the keys 19 remain in the sockets of their respective teeth 17. The retentive knob attachment portion of the keys extends from the base of each tooth and with the platform portion of the key in intimate contact with the base of the tooth. The matrix-supported keyed teeth are then held in juxtaposition with the implant connectors of the patient modeling.

Figure 10A:
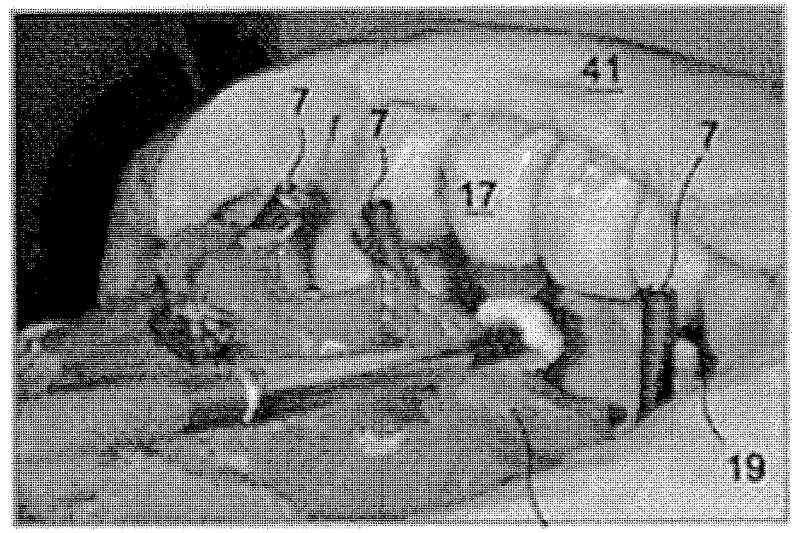
FIG. 10a is a left side top rear isometric view showing the keyed teeth molded into the horizontal beam supported by the matrix.
Figure 10B:
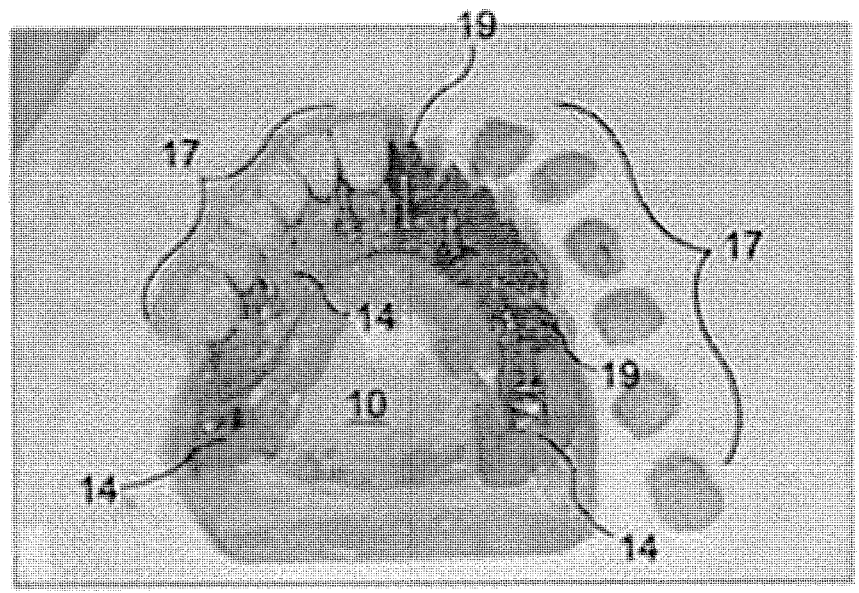
FIG. 10b is a top rear isometric view of the horizontal beam, keyway teeth and keys on the module with the matrix removed.
Figure 11A:
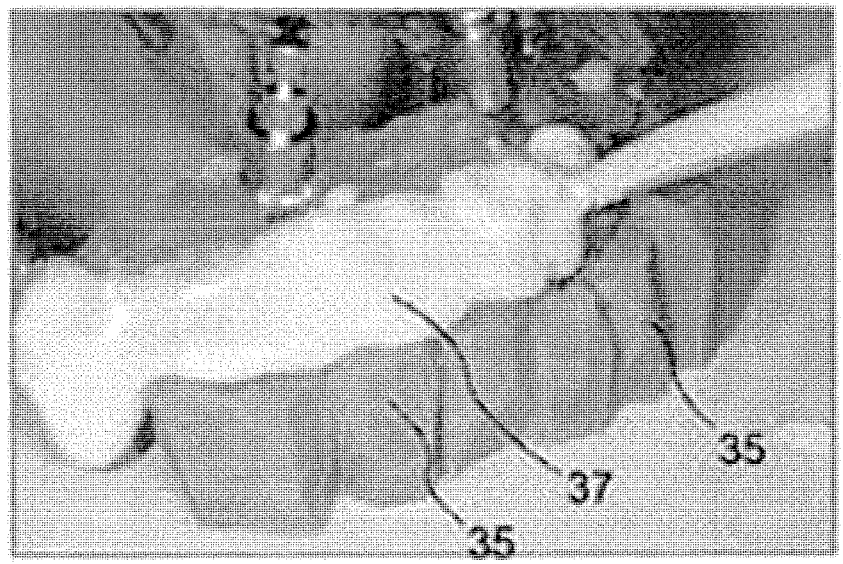
FIGS. 11a, 11b, 11c and 11d are isometric views showing the use of key protector caps in completing the horizontal beam portion of the framework pattern.
Figure 11B:
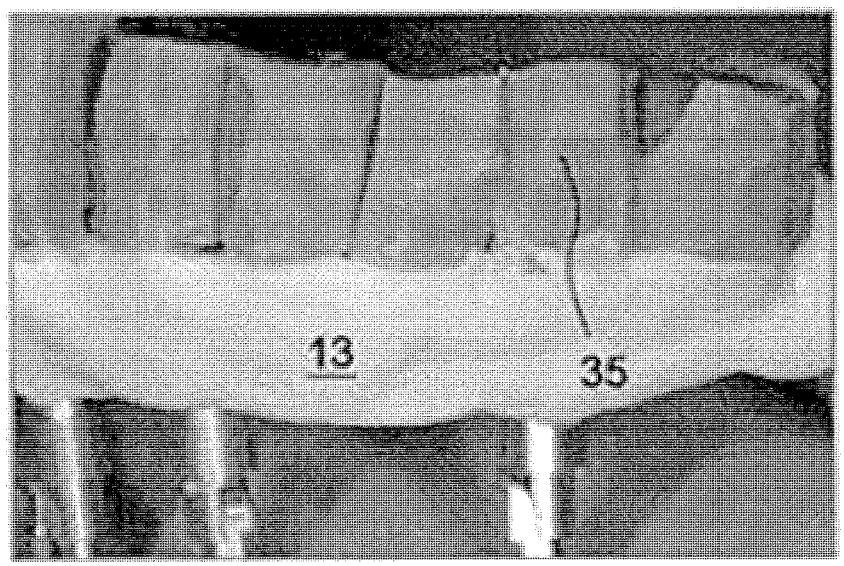
Figure 11C:
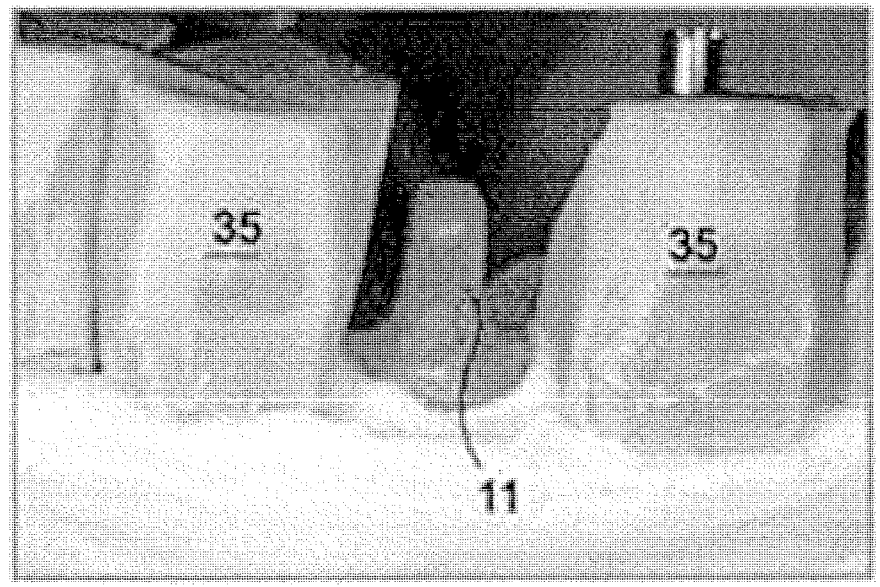
Figure 11D:
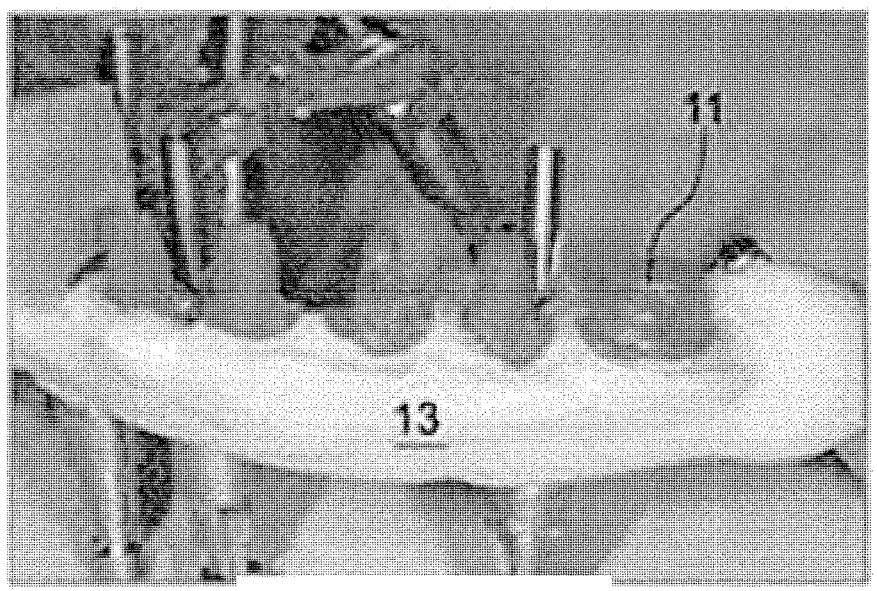

Referring now to FIG. 10a, the retentive knobs of the keys are then joined to the implant prosthetic cylinders and to one another during the formation of the intermediate horizontal beam and supported in the setup location by the matrix 41 on the model. After the resin is set, the matrix is removed as shown in FIG. 10b. Half of the teeth in this illustration are removed to reveal the pattern keys.

Referring now to FIG. 11, the process continues with more modifiable resin material added to complete the horizontal beam portion of the framework using protective caps 35 as shown in FIGS. 11a, 11b, 11c and 11d. The protective caps 35 are installed on the keys 11 prior to the addition of the additional material 37 used to reinforce and contour the horizontal beam. The purpose of the protective caps is to prevent contamination of the keys by excess resin which could distort the pattern and prevent complete seating of the tooth on the final framework.

Figure 12A:
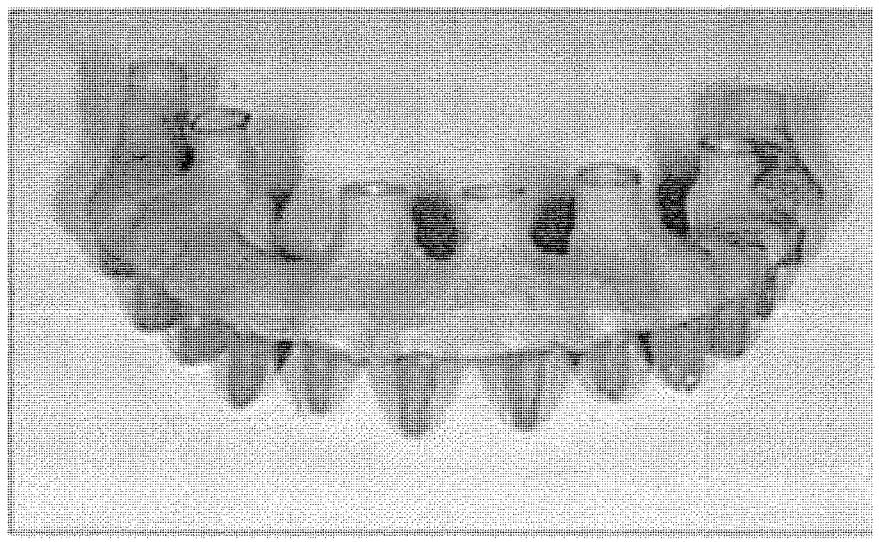
FIG. 12a depicts a completed framework pattern.
Figure 12B:
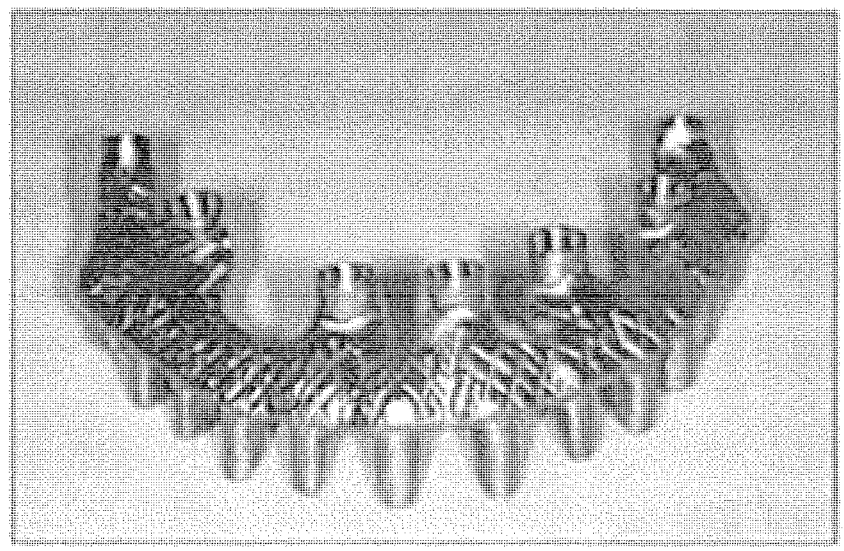

The horizontal beam assembly 13 is then removed from the model and the teeth removed from the keys. The remaining structure is refined providing the pattern depicted in FIG. 12a for constructing the final framework shown in FIG. 12b which can be constructed from the pattern using a variety of methods, such as:

a) Traditional lost wax technique where the framework pattern is invested, burned out and metal is cast into the mold, or b) Copy milling using scanning technology where the framework pattern is scanned and data files are developed and transmitted to robotic milling machines for the milling of the final framework from a variety of solid materials (metal or ceramic by example).

As an option, the above-described procedure following the finished setup can be replaced by more advanced technology which permits the virtual construction of the framework from an optical scanning of the finished setup. In concert with the use of computer software which includes the three-dimensional characteristics of virtual keys that correspond to the individual scanned teeth in the setup, the location and orientation of the keys is then combined with a framework pattern that creates a file which is then copy milled by a CNC milling machine to create the final framework.

When prosthetic retention screws have their access channel coming through any portion of the keyway tooth, that tooth (either in wax or green state) will be manually or virtually modified to permit screwdriver access to the head of the screw. Acrylic, wax and green state keyway teeth may be modified or customized to accommodate the opposing occlusion, or individual cosmetic patient requirements.

Figure 13:
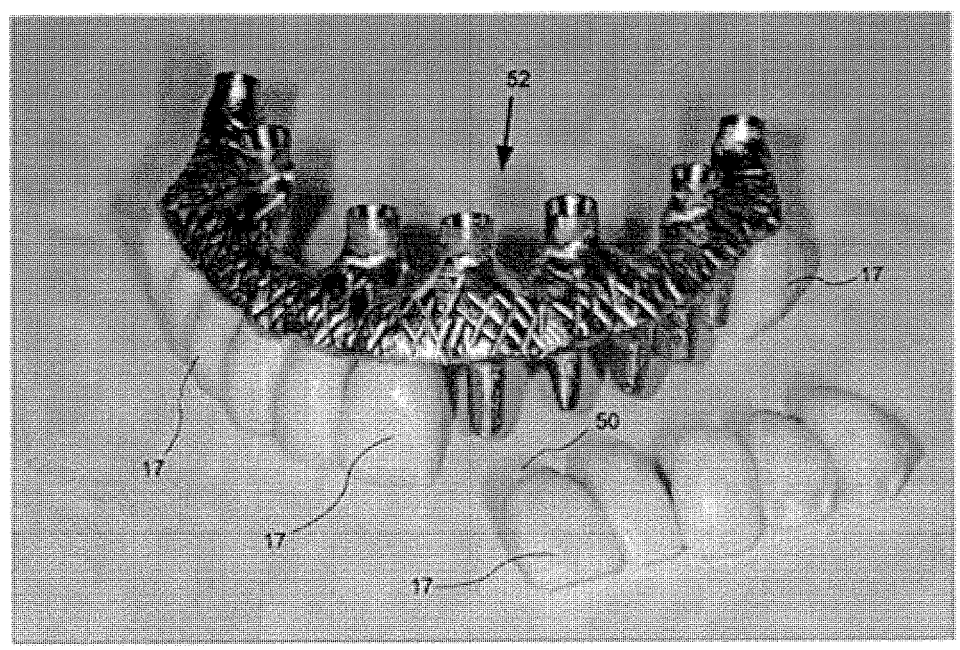
FIG. 13 is an isometric assembly view of the teeth being assembled to the completed framework.
Figure 14:
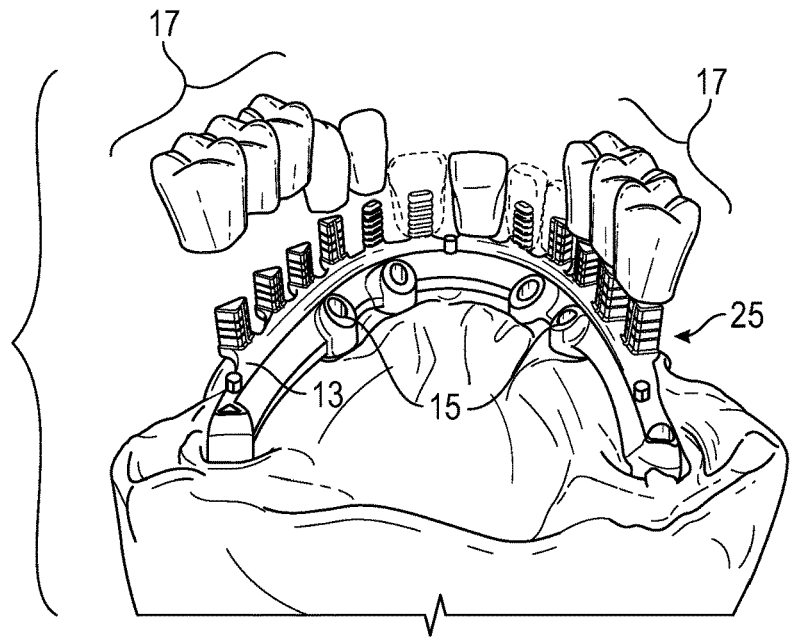
FIG. 14 is an exploded view from the anterior side of inventive key used in the framework system.
Figure 15:
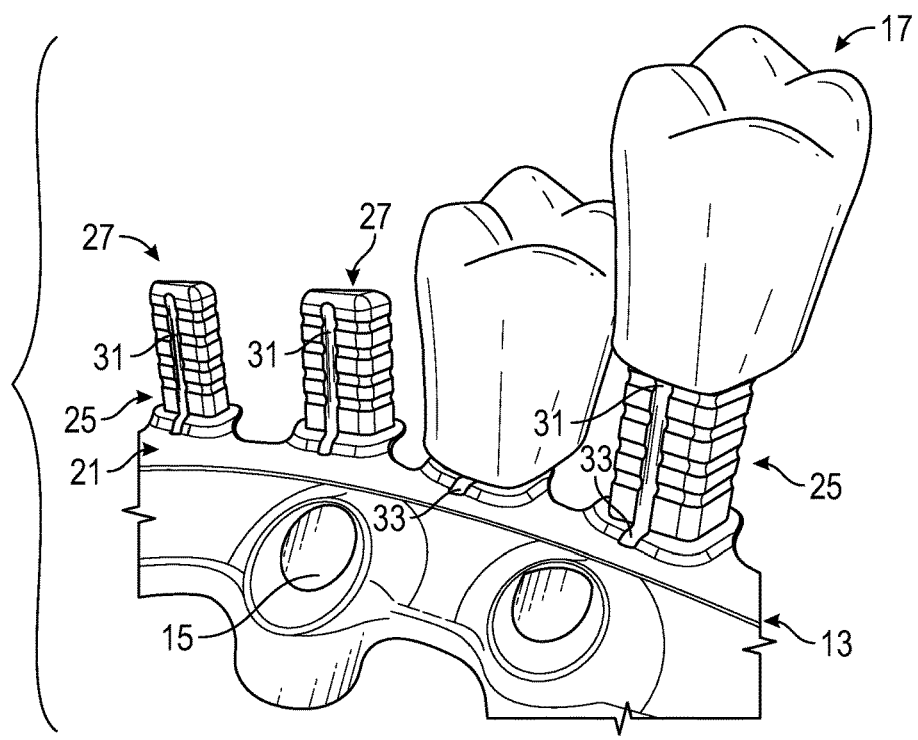
FIG. 15 shows an embodiment of the keyway system from 14, with an isolated view of the key being mounted with a prosthetic tooth.
Figure 16:
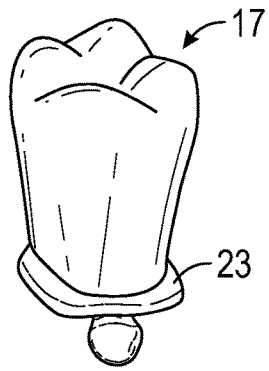
FIGS. 16-18 illustrates an embodiment of invention depicting side, top and perspective views of an inventive key.
Figure 17:
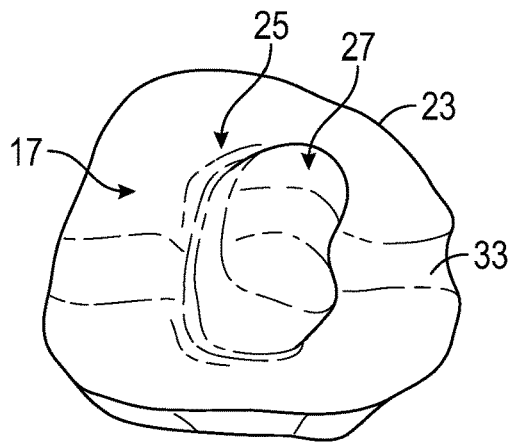
Figure 18:
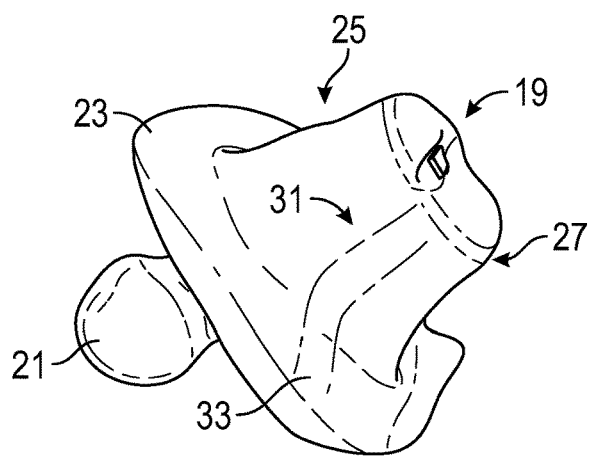

With the final framework 52 completed, the selected teeth are cemented to the metal or ceramic framework as shown in FIG. 13 and the gingival veneering material is then applied to complete the prosthesis construction. A cervical groove 50 in the keyway tooth will be covered with the gingival veneering material, providing additional stability and retention of the tooth to the final framework.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. For example, this invention can be applied to totally or partially edentulous patients being restored with osseointegrated dental implants.

What is claimed as being new and desired to be protected by Letters Patent of the United States is as follows:

1. A free-standing one-piece key utilized in forming a pattern for a prosthetic framework strut that may be affixed upon one or more implants or implant abutments within a prosthetic tooth, the key comprising:
- a shaft having a coronal aspect at a coronal end of the shaft for placing the prosthetic tooth;
- a retention knob at an opposite end of the coronal end, the retention knob having a spheroid shape and a diameter greater than that of the shaft; and
- a cervical platform between the retention knob and the coronal end, and comprising a supporting base of the key.

2. The key of claim 1 wherein said key includes an elongate channel extending along a surface of the shaft to the cervical platform for the expulsion of excess adhesive fluid.

3. The key of claim 2 wherein said channel is an axial groove that forms a release opening at a margin between the tooth and the cervical.

4. The key of claim 3 wherein said shaft is tapered from said platform toward the coronal aspect of the key.

5. The key of claim 2, the channel forming a release opening at a margin between the tooth and the cervical platform.

6. The key of claim 1 wherein the spheroid is asymmetrical.

7. The key of claim 1, the shaft resembling a triangular prism.

8. The key of claim 1, wherein the shaft at the coronal end is configured to fit within an axial internal keyway of a socket of a tooth.

9. The key of claim 1 wherein the spheroid is irregular.

10. A vertical strut component to be disposed between a prosthetic framework model and a socket of a prosthetic tooth, the strut comprising:
- an elongate shaft having a coronal aspect at a first end of the shaft for placing the prosthetic tooth;
- a retentive element having a spheroid shape at a second end of the shaft, wherein the retentive element having a diameter greater than that of the shaft; and the coronal aspect being configured to lock within an axial internal keyway of a socket of the tooth,
- a cervical platform between the first and second end being configured to support a cervical aspect of the prosthetic tooth; and
- an elongate channel extending along a surface of the shaft to the cervical platform for an expulsion of excess adhesive fluid, wherein said channel is an axial groove that forms a release opening at a margin between the tooth and the cervical platform.

11. The vertical strut component in claim 10, wherein the spheroid is asymmetrical.

12. The key of claim 10 wherein the spheroid is asymmetrical.

13. They key of claim 8, wherein the shaft tapers between the cervical platform and the coronal aspect.

14. The key of claim 13, wherein the shaft resembles a triangular prism.

15. The key of claim 10, wherein the spheroid is irregular.

* * * * *